United States Patent [19]

Boisde et al.

[11] 4,225,232

[45] Sep. 30, 1980

[54] PHOTOMETRIC CELL

[75] Inventors: Gilbert Boisde, Bures-sur-Yvette; Alain Boissier, Marly le Roi, both of France

[73] Assignee: Commissariat a l'Energie Atomique, Paris, France

[21] Appl. No.: 21,698

[22] Filed: Mar. 19, 1979

[30] Foreign Application Priority Data

Mar. 30, 1978 [FR] France .............................. 78 09256

[51] Int. Cl.³ .............................................. G01N 1/10
[52] U.S. Cl. .................................... 356/246; 356/440
[58] Field of Search ................................ 356/246, 440

[56] References Cited

U.S. PATENT DOCUMENTS 3,861,809 1/1975 Hall, Jr. ........................... 356/246 X

FOREIGN PATENT DOCUMENTS 2307298 8/1973 Fed. Rep. of Germany .......... 356/246

OTHER PUBLICATIONS

Biernacki et al., "A Long Path Length, Low Temperature Multiple Traversal Cell" Applied Spectroscopy, vol. 26, No. 6, pp. 648–650, Dec. 1972.
White, "Long Optical Paths of Large Aperture" *J. Opt. Soc. Am.*, vol. 32 No. 4, pp. 285–288, May 1942.

*Primary Examiner*—John K. Corbin
*Assistant Examiner*—Matthew W. Koren
*Attorney, Agent, or Firm*—Frishauf, Holtz, Goodman & Woodward

[57] ABSTRACT

Photometric cell of the type comprising two juxtaposed spherical half-mirrors $M_1$ and $M_2$ and a third spherical mirror M facing mirrors $M_1$ and $M_2$, the three mirrors having the same radius of curvature, while mirrors $M_1$ and $M_2$ have their centers of curvature $C_1$ and $C_2$ located on mirror M and slightly displaced with respect to one another and mirror M has its center of curvature C between the two mirrors $M_1$ and $M_2$, optical means being provided for introducing a measuring light beam into the cell through an entrance diaphragm E and for extracting it therefrom after multiple reflections on said mirrors through an exit diaphragm S, wherein the mirror M is truncated perpendicular to a line joining the centers $C_1$ and $C_2$, the truncated portion of the mirror being replaced by an optical system L operating by transmission, the entrance diaphragm E and exit diaphragm S being positioned level with said optical system L on a line perpendicular to lines $C_1$–$C_2$, and wherein it also comprises a third half-mirror $M_3$, the optical system L being such that the half-mirrors $M_1$ and $M_2$ are conjugate to one another, while the third half-mirror $M_3$ has a center of curvature $C_3$ located on the line joining the two diaphragms E and S conjugate to one another by the mirrors and the optical system L.

3 Claims, 6 Drawing Figures

PHOTOMETRIC CELL

BACKGROUND OF THE INVENTION

The present invention relates to a photometric cell and is applied to the measurement of the optical density of fluids (for example liquid) and in particular to the measurement of the turbidity of river water or nuclear reactor water or to the detection of pollutants in liquids or gases.

Photometers are known which comprise a vessel containing the fluid to be analysed and optical means for passing a beam of light through the said vessel. The measurement of the attenuation due to the traversal of the vessel makes it possible to calculate the optical density of the fluid and the concentration of one of the substances present in the fluid.

Although such devices are suitable in certain cases they have the disadvantage of having a limited optical path for the light beam which limits their accuracy. Therefore devices having two generally spherical mirrors have been proposed, said mirrors being arranged on either side of the vessel in such a way that the light beam can pass to and fro between the mirrors and the optical path is lengthened for the same overall dimensions.

The photometric cell closest to that of the present invention is the so-called White cell, described more particularly in the Article by J. U. White, published in the J.O.S.A. Journal, Vol. 32, p 285 May 1942 and entitled "Long Optical Paths of Large Aperture."

Such a cell is diagrammatically shown in FIG. 1 and comprises two juxtaposed spherical half-mirrors $M_1$ and $M_2$ and a third spherical mirror M facing mirrors $M_1$ and $M_2$. The three mirrors have the same radius of curvature. Mirrors $M_1$ and $M_2$ have their centre of curvature $C_1$ and $C_2$ located on mirror M and slightly staggered relative to one another. The centre of curvature C of mirror M is disposed between the two half-mirrors $M_1$ and $M_2$. The light beam used for performing the measurement penetrates the cell by means of an entrance diaphragm E and leaves the cell after multiple reflections on the mirrors by an exit diaphragm S, said two diaphragms being disposed in openings made in the mirror M.

The operating principle of this device is illustrated by the diagram of FIG. 2 which shows mirror M viewed from the front and the images formed with it. On the basis of the Standard Laws of Optics it is known that the image of an object point located in the vicinity of the centre of curvature of a spherical mirror is an image point such that the centre of curvature, as a first approximation, is the centre of the segment formed by the object point and the image point. Thus, the entrance diaphragm E considered as an object $I_0$ gives, after a first reflection in the half-mirror $M_1$ a symmetrical image $I_1$ of $I_0$ with respect to the centre $C_1$. In turn this image $I_1$, by reflection on the second half-mirror $M_2$ gives a second symmetrical image $I_2$ of $I_1$ with respect to the centre of curvature $C_2$ of the second half-mirror and so on. Thus, as a result of multiple reflections on the mirrors a sequence of images is obtained, all of which differ from one another and substantially located in the plane defined by the centres of curvature and the entrance diaphragm, i.e. on mirror M. These images are all aligned on two straight lines parallel to the line joining the centres of curvature $C_1$ and $C_2$. The exit diaphragm S is positioned in such a way that it coincides with one of these images (with the eleventh image $I_{11}$ in FIG. 2). In other words the entrance and exit diaphragms are optically conjugated by the mirrors after a large number of reflections.

It is clear that such a device leads to a relatively large optical path because the number of reflections y is high (in the example of FIG. 2 the light beam traverses the cell 22 times during the 11 to and fro movements).

BRIEF SUMMARY OF THE INVENTION

The cell according to the present invention provides an improvement of the known device because it makes it possible to significantly increase the optical path by multiplying it by 2, 3 or more. To this end instead of extracting the light beam when it again reaches the periphery of mirror M (at $I_{11}$ in FIG. 2) it is passed into a cell of another type having a pair of conjugate mirrors in order to reintroduce the light beam into the White cell where it again undergoes a large number of reflections.

More specifically the present invention relates to a photometric cell of the type comprising two juxtaposed spherical half-mirrors $M_1$ and $M_2$ and a third spherical mirror M facing mirrors $M_1$ and $M_2$, the three mirrors having the same radius of curvature, whilst mirrors $M_1$ and $M_2$ have their centres of curvature $C_1$ and $C_2$ located on mirror M and slightly displaced with respect to one another and mirror M has its centre of curvature C between the two mirrors $M_1$ and $M_2$, optical means being provided for introducing a measuring light beam into the cell through an entrance diaphragm E and for extracting it therefrom after multiple reflections on said mirrors through an exit diaphragm S, wherein the mirror M is truncated perpendicular to a line joining the centres $C_1$ and $C_2$, the truncated portion of the mirror being replaced by an optical system L operating by transmission, the entrance diaphragm E and exit diaphragm S being positioned level with said optical system L on a line perpendicular to lines $C_1$–$C_2$, and wherein it also comprises a third half-mirror $M_3$, the optical system L being such that the half-mirrors $M_1$ and $M_3$ are conjugate to one another, whilst the third half-mirror $M_3$ has a centre of curvature $C_3$ located on the line joining the two diaphragms E and S conjugate to one another by the mirrors and the optical system L.

The term "slightly displaced centres of curvature" is understood to mean centres spaced from one another by a small distance compared with the radii of curvature of the mirrors and for example less than a tenth of said radii in such a way that the system functions in Gaussian optics.

Although it is possible to use any optical system able to introduce a light beam between two mirrors or to extract it therefrom (for example prism or lens systems or laser and deflector systems) preference is given to the use of light guides comprising pipes or optical fibres for constituting such members.

BRIEF DESCRIPTION OF THE DRAWINGS

The invention will be described in greater detail hereinafter relative to non-limitative embodiments and with reference to the attached drawings, wherein show.

DETAILED DESCRIPTION OF THE PREFERRED EMBODIMENTS

Figure 1:
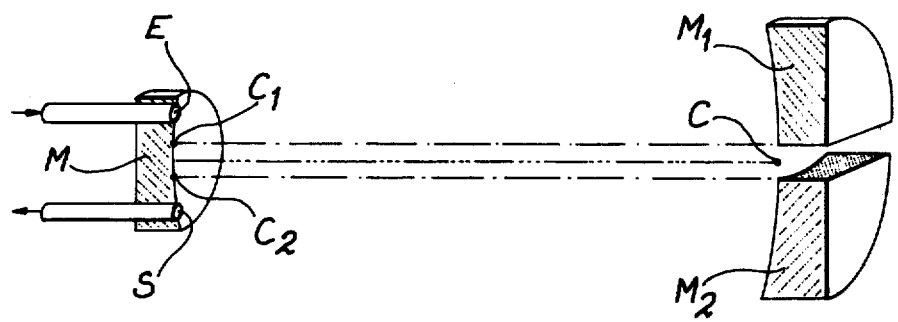
FIG. 1 diagrammatically a prior art cell.
Figure 2:
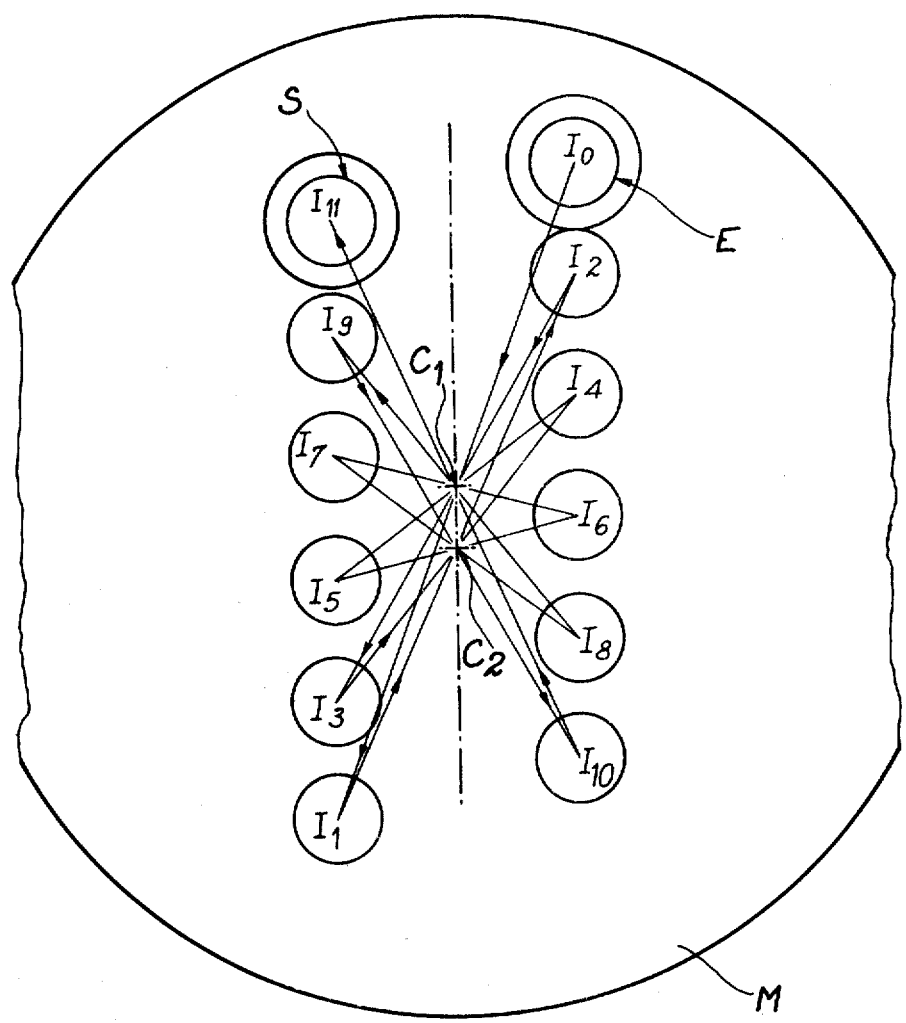
FIG. 2 a diagram explaining the operation of the prior art cell.

FIGS. 1 and 2 have already been described in connection with the prior art.

Figure 3:
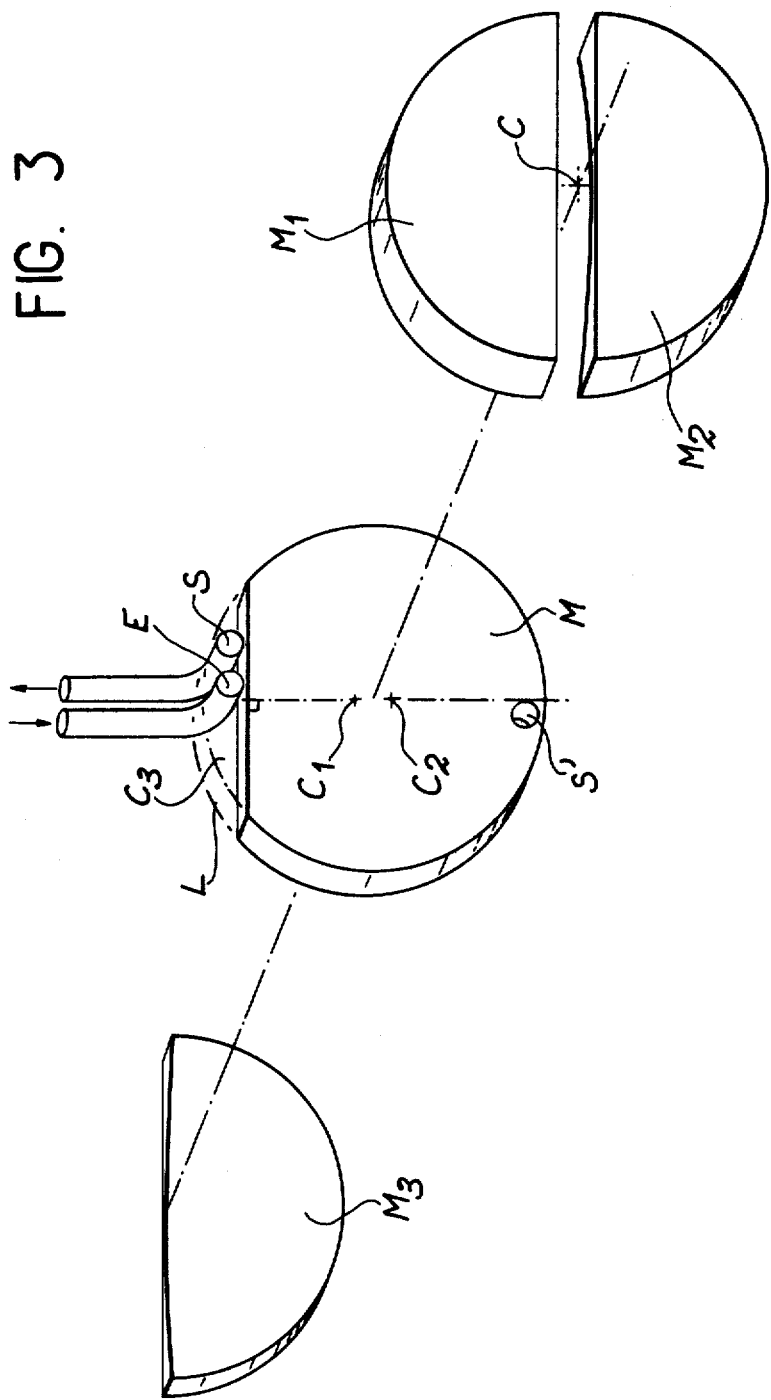
FIG. 3 diagrammatically the essential optical means of a cell according to the invention.

FIG. 3 shows the essential means of a photometric cell according to the invention. Such a cell comprises, like the White cell, two spherical half-mirrors $M_1$ and $M_2$, whose centres of curvature $C_1$ and $C_2$ are slightly displaced with respect to one another and located on a spherical mirror M, whose centre of curvature C is located between the two half-mirrors $M_1$ and $M_2$.

According to the invention mirror M is truncated perpendicular to the line joining $C_1$ and $C_2$, i.e. horizontally in the case of FIG. 3. The truncated portion of the mirror is replaced by an optical system L working by transmission. A supplementary half-mirror $M_3$ is positioned behind optical system L. The focal distance of optical system L and the position of $M_3$ are such that the two half-mirrors $M_1$ and $M_3$ are conjugate. The light beam is introduced into the cell and extracted from the cell by entrance diaphragm E and exit diaphragm S located in openings made in the optical system L, the line joining E and S being perpendicular to the line joining $C_1$ and $C_2$. Moreover half-mirror $M_3$ has its centre of curvature $C_3$ in optical system L on the line joining E and S.

Figure 4:
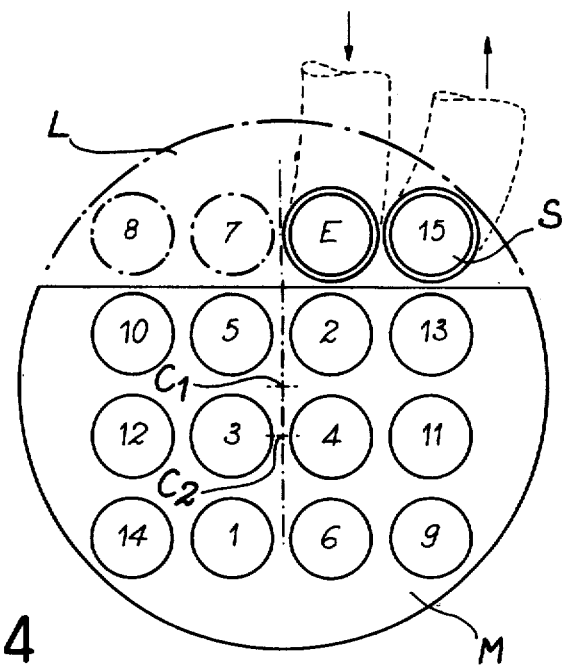
FIG. 4 a diagram explaining the operation of the cell of FIG. 3.

The operation of this cell is illustrated by FIG. 4. The part of the cell between the truncated mirror M and the two half-mirrors $M_1$ and $M_2$ behaves in the manner of a pseudo-White cell. The light beam y enters it through diaphragm E and gives rise to successive images 1, 2, 3 . . . 6, 7, which are such that two successive images define a segment, whose centre is formed by one of the centres $C_1$ or $C_2$. All these images are distributed along two straight lines parallel to line $C_1$–$C_2$ joining the centres of curvature of $M_1$ and $M_2$. These straight lines are positioned on either side of lines $C_1$–$C_2$.

The last of these images, 7 in FIG. 4, drops on optical system L, but not on the exit diaphragm S, which differentiates this part of the cell from the true White cell. The light beam passes out from the space defined by mirrors $M_1$, $M_2$ and M and spreads towards mirror $M_3$. The image given by half-mirror $M_3$ of image 7 is an image 8 such that the centre of segment 7–8 is centre $C_3$. Thus, the light beam is reintroduced into the White cell at 8, which behaves like a further entrance diaphragm leading to a further group of images distributed along the two straight lines parallel to lines $C_1$–$C_2$ and on either side of the latter, said images being numbered 9, 10, 11 . . . 15 in FIG. 4. The final image (15 in FIG. 4) coincides with the exit diaphragms S of the cell, which is possible because the centre of curvature $C_3$ is on the line of diaphragms E and S.

Thus, the detour via rear half-mirror $M_3$ permits in the illustrated embodiment the multiplication by two of the path of the light beam in the pseudo-White cell.

Figure 5:
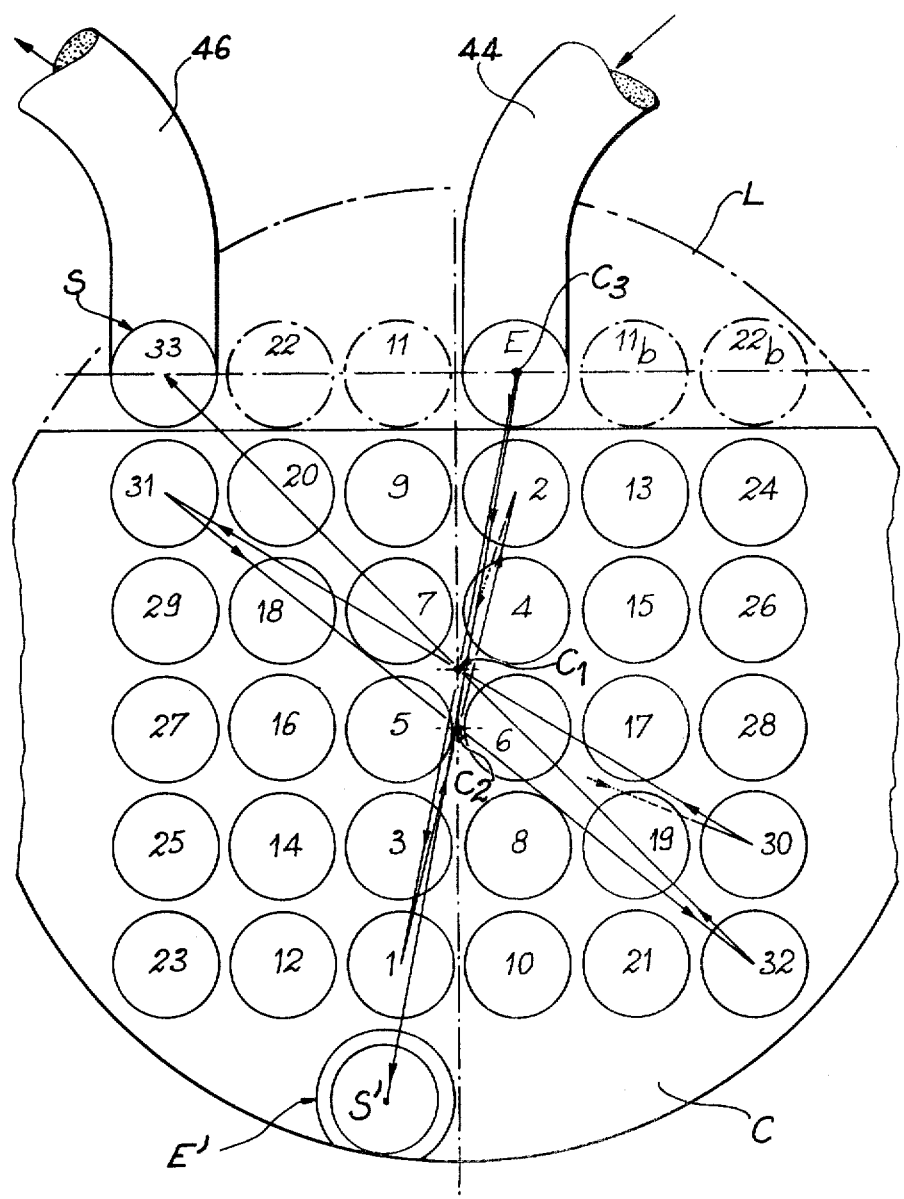
FIG. 5 another diagram explaining the operation of an improved variant of the cell of the invention.

Obviously further increases in this path are possible through a careful selection of the relative position of centre of curvature $C_3$ and exit diaphragm S. FIG. 5, for example, illustrates a variant in which the centre of curvature $C_3$ is level with the entrance diaphragm E in such a way that the final image 11 of the first group gives rise, after reflection on half-mirror $M_3$, to a symetrical image 11b of 11 with respect to $C_3$, said image being at the head of a new group which is completed by image 22 giving, after reflection on mirror $M_3$, an image 22b which is the head of a third group of images terminating with image 33 and this forms the location for exit diaphragm S.

It has been apparent from FIG. 5 that the images given by the pseudo-White cell constituted by truncated mirror M and the two mirrors $M_1$ and $M_2$ are distributed along vertical lines, whilst the images given by the cell constituted by the two half-mirrors $M_3$ and $M_2$ and optical system L are distributed along a horizontal line.

Reference can for example be made to French patent application No. 7714753, filed on May 13th 1977 and entitled "Photometer with concave mirrors and field optics" in connection with photometric cells constituted by two spherical mirrors conjugated by a transmission optical system.

For a given vessel length and for diaphragms and a mirror M of given diameters the optical arrangement of the intermediate images is a figure which can be inscribed in a square. Moreover the number of "columns" of images in a White cell is necessarily even of the form 2N with N>2. The optimum number of images formed on the mirror M of the cell according to the invention is therefore of the form $n=(2N)^2$. In the case of the varient of FIG. 4 we have N=2 and n=16 and for that of FIG. 5 N=3 and n=36.

In certain cases the arrangement "in a square" may lead to inadequate flexibility when it is a question of adjusting the optical path length. If necessary, it is naturally possible to use "in rectangle" arrangements with a number of columns 2N differing from the number of lines J.

The following Table gives numerical values for the main geometrical characteristics of the cells according to a number of embodiments. The unit of length is the millimeter in the following Table, in which the symbols have the following meanings:

2N: number of columns of images on mirror M
J: number of lines of images on mirror M
n: total number of images on mirror M
l: distance between mirror M and mirrors $M_1/M_2$
d: diameter of mirror M
P: optical path in cell
D: diameter of half-mirrors $M_1$ and $M_2$
V: internal volume of the analytical cell (in milliliters)

| 2N | J | n  | P     | l   | d  | D  | V ml | T air | T water |
|----|---|----|-------|-----|----|----|------|-------|---------|
| 4  | 4 | 16 | 4536  | 162 | 28 | 54 | 221  | 0.27  | 0.34    |
| 4  | 5 | 20 | 6192  | 172 | 30 | 57 | 364  | 0.26  | 0.32    |
| 4  | 6 | 24 | 8844  | 201 | 35 | 67 | 425  | 0.23  | 0.29    |
| 6  | 5 | 30 | 11502 | 213 | 37 | 71 | 504  | 0.19  | 0.25    |
| 6  | 6 | 36 | 16038 | 243 | 42 | 81 | 746  | 0.16  | 0.22    |

This Table corresponds to an entrance diaphragm diameter of 5 millimeters and a light beam divergence of 20°. Under the same conditions and for an optical path of about 11 meters the dead volume of the White cell is 1144 milliliters, whereas in the case of the present invention it is only 504 milliliters, which clearly shows the interest of the present device. Moreover this interest increases with the optical path length, which justifies the construction of cells with very long paths.

The coefficient of light transmission T through the cell according to the invention is dependent on:
- the transmission coefficient $T_1$ for one reflection on a mirror and a number $n_1$ of reflections;
- the transmission coefficient $T_2$ for an air—glass passage and a number $n_2$ of said passages;
- the transmission coefficient $T_3$ for a fluid to be analysed—glass passage and a number $n_3$ of said passages.

Thus, the overall transmission coefficient is:
$T = T_1^{n_1} \times T_2^{n_2} \times T_3^{n_3}$.

The above Table gives two series of values for this transmission coefficient in the case where the cell is filled with air (i.e. coefficient $T_{air}$) and in the case where it is filled with water ($T_{water}$).

It is also apparent that when the two mirrors $M_1$ and $M_2$ are illuminated simultaneously that a first reflection on half-mirror $M_2$ gives rise to a first symmetrical image $E'$ of E with respect to the centre of curvature $C_2$ (cf FIG. 5). An auxiliary opening $S'$ made in mirror M at this location optionally permits the use of the emergent light beam for a small optical path analysis. Operating with two different wavelengths of the absorption spectrum this system also makes it possible to eliminate the turbidity residue of the fluid to be analysed.

Figure 6:
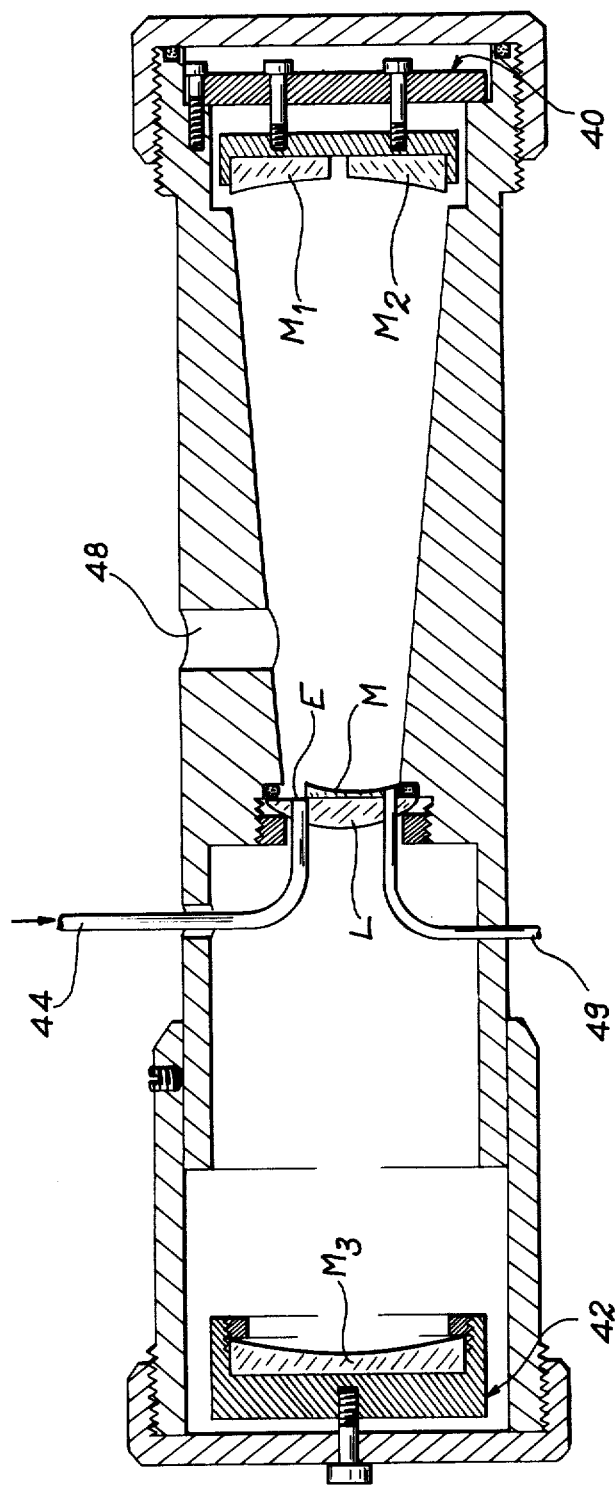
FIG. 6 a longitudinal section through a cell according to the invention.

FIG. 6 diagrammatically shows a longitudinal section through a photometric cell according to the invention. It is possible to see the two half-mirrors $M_1$ and $M_2$, the truncated mirror M, mirror $M_3$ (which is in this case a complete mirror of which only the lower half is used) and the optical system L (which is a complete lens, but only its upper portion is used).

FIG. 6 also shows means 40 for regulating mirrors $M_1$ and $M_2$, means 42 for regulating mirror $M_3$, a light guide 44 for introducing the light beam through entrance diaphragm E, another guide being provided for the extraction of the light which is not visible in FIG. 6 but which appears on FIG. 5. An optional guide 49 serves to extract the light reflected on mirror $M_2$ after a single to and fro travel in the analytical cell. The cell also comprises an opening 48 for the introduction of the fluid to be measured which, in the illustrated variant, occupies the volume between mirror M and the half-mirrors $M_1$ and $M_2$.

The invention is not limited to the embodiments described and represented hereinbefore and various modifications can be made thereto without passing beyond the scope of the invention.

What is claimed is:

1. A photometric cell of the type comprising two juxtaposed spherical half-mirrors $M_1$ and $M_2$ and a third spherical mirror M facing mirrors $M_1$ and $M_2$, the three mirrors having the same radius of curvature, whilst mirrors $M_1$ and $M_2$ have their centres of curvature $C_1$ and $C_2$ located on mirror M and slightly displaced with respect to one another and mirror M has its centre of curvature C between the two mirrors $M_1$ and $M_2$, optical means being provided for introducing a measuring light beam into the cell through an entrance diaphragm E and for extracting it therefrom after multiple reflections on said mirrors through an exit diaphragm S, wherein the mirror M is truncated perpendicular to a line joining the centres $C_1$ and $C_2$, the truncated portion of the mirror being replaced by an optical system L operating by transmission, the entrance diaphragm E and exit diaphragm S being positioned level with said optical system L on a line perpendicular to lines $C_1$-$C_2$, and wherein it also comprises a third half-mirror $M_3$, the optical system L being such that the half-mirrors $M_1$ and $M_3$ are conjugate to one another, whilst the third half-mirror $M_3$ has a centre of curvature $C_3$ located on the line joining the two diaphragms E and S conjugate to one another by the mirrors and the optical system L.

2. A photometric cell according to claim 1, wherein the means for introducing and extracting the light beam comprise light guides and in particular optical fibres.

3. A photometric cell according to claim 1, wherein it comprises means for introducing a fluid to be measured between the mirror M and the two half-mirrors $M_1$-$M_2$.

* * * * *